United States Patent
McKenzie (12)

(10) Patent No.: US 6,316,705 B1
(45) Date of Patent: Nov. 13, 2001

(54) RICE CULTIVAR CALHIKARI-201

(75) Inventor: Kent S. McKenzie, Oroville, CA (US)

(73) Assignee: California Cooperative Rice Research Foundation Inc, Biggs, CA (US)

( * ) Notice: Subject to any disclaimer, the term of this patent is extended or adjusted under 35 U.S.C. 154(b) by 0 days.

(21) Appl. No.: 09/488,560

(22) Filed: Jan. 21, 2000

(51) Int. Cl.$^7$ ............................... A01H 5/00; A01H 5/10; A01H 4/00; A01H 1/04; C12N 5/04
(52) U.S. Cl. ..................... 800/320.2; 800/260; 800/300; 800/301; 800/302; 800/303; 435/410; 435/430
(58) Field of Search ..................... 800/320.2, 298, 800/303, 301, 302, 300, 260, 271, 274; 435/410, 430

(56) References Cited

PUBLICATIONS

Plant Variety Protection Certificate No. 8900034 for Rice Cultivar S–101, issued Nov. 30, 1992.

*Primary Examiner*—Gary Benzion
*Assistant Examiner*—Melissa L. Kimball
(74) *Attorney, Agent, or Firm*—Rothwell, Figg, Ernst & Manbeck

(57) ABSTRACT

A novel rice cultivar, designated Calhikari-201, is disclosed. The invention relates to the seeds of rice cultivar Calhikari-201, to the plants of rice Calhikari-201 and to methods for producing a rice plant produced by crossing the cultivar Calhikari-201 with itself or another rice variety. The invention further relates to hybrid rice seeds and plants produced by crossing the cultivar Calhikari-201 with another rice cultivar.

23 Claims, No Drawings

RICE CULTIVAR CALHIKARI-201

BACKGROUND OF THE INVENTION

The present invention relates to a new and distinctive rice cultivar, designated Calhikari-201. Rice is an ancient agricultural crop and is today one of the principal food crops of the world. There are two cultivated species of rice: *Oryza sativa* L., the Asian rice, and *O. glaberrima* Steud., the African rice. *O. sativa* L. constitutes virtually all of the world's cultivated rice and is the species grown in the United States. Three major rice producing regions exist in the United States: the Mississippi Delta (Arkansas, Mississippi, northeast Louisiana, southeast Missouri), the Gulf Coast (southwest Louisiana, southeast Texas), and the Central Valleys of California.

Rice is a semiaquatic crop that benefits from flooded soil conditions during part or all of the growing season. In the United States, rice is grown on flooded soils to optimize grain yields. Heavy clay soils or silt loam soils with hard pan layers about 30 cm below the surface are typical rice-producing soils because they minimize water losses from soil percolation. Rice production in the United States can be broadly categorized as either dry-seeded or water-seeded. In the dry-seeded system, rice is sown into a well-prepared seed bed with a grain drill or by broadcasting the seed and incorporating it with a disk or harrow. Moisture for seed germination is from irrigation or rainfall. Another method of planting by the dry-seeded system is to broadcast the seed by airplane into a flooded field, then promptly drain the water from the field. For the dry-seeded system, when the plants have reached sufficient size (four- to five-leaf stage), a shallow permanent flood of water 5 to 16 cm deep is applied to the field for the remainder of the crop season.

In the water-seeded system, rice seed is soaked for 12 to 36 hours to initiate germination, and the seed is broadcast by airplane into a flooded field. The seedlings emerge through a shallow flood, or the water may be drained from the field for a short period of time to enhance seedling establishment. A shallow flood is maintained until the rice approaches maturity. For both the dry-seeded and water-seeded production systems, the fields are drained when the crop is mature, and the rice is harvested 2 to 3 weeks later with large combines. In rice breeding programs, breeders try to employ the production systems predominant in their respective region. Thus, a drill-seeded breeding nursery is used by breeders in a region where rice is drill-seeded and a water-seeded nursery is used in regions where water-seeding is important.

Rice in the United States is classified into three primary market types by grain size, shape, and chemical composition of the endosperm: long-grain, medium grain and short-grain. Typical U.S. long-grain cultivars cook dry and fluffy when steamed or boiled, whereas medium- and short-grain cultivars cook moist and sticky. Long-grain cultivars have been traditionally grown in the southern states and generally receive higher market prices.

Although specific breeding objectives vary somewhat in the different regions, increasing yield is a primary objective in all programs. Grain yield of rice is determined by the number of panicles per unit area, the number of fertile florets per panicle, and grain weight per floret. Increases in any or all of these yield components may provide a mechanism to obtain higher yields. Heritable variation exists for all of these components, and breeders may directly or indirectly select for increases in any of them.

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety an improved combination of desirable traits from the parental germplasm. These important traits may include higher seed yield, resistance to diseases and insects, better stems and roots, tolerance to low temperatures, and better agronomic characteristics or grain quality.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, recurrent selection, or a combination of these methods.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for three or more years. The best lines are candidates for new commercial cultivars; those still deficient in a few traits may be used as parents to produce new populations for further selection.

These processes, which lead to the final step of marketing and distribution, usually take from eight to 12 years from the time the first cross is made and may rely on the development of improved breeding lines as precursors. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of plant breeding is to develop new, unique and superior rice cultivars and hybrids. The breeder initially selects and crosses two or more parental lines, followed by self-pollination and selection, producing many new genetic combinations. The breeder can theoretically generate billions of different genetic combinations via crossing, selfing and mutations. The breeder has no direct control at the cellular level. Therefore, two breeders will never develop the same line, or even very similar lines, having the same rice traits.

Each year, the plant breeder selects the germplasm to advance to the next generation. This germplasm is grown under unique and different geographical, climatic and soil conditions, and further selections are then made, during and at the end of the growing season. The cultivars which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same cultivar twice by using the exact same original parents and the same selection techniques. This unpredictability results in the expenditure of large amounts of research monies to develop superior new rice cultivars.

The development of new rice cultivars requires the development and selection of rice varieties, the crossing of these varieties and selection of superior hybrid crosses. The hybrid seed is produced by manual crosses between selected male-fertile parents or by using male sterility systems. These hybrids are selected for certain single gene traits such as semidwarf plant type, pubescence, awns, and apiculus color which indicate that the seed is truly a hybrid. Additional data on parental lines, as well as the phenotype of the hybrid, influence the breeder's decision whether to continue with the specific hybrid cross.

Pedigree breeding and recurrent selection breeding methods are used to develop cultivars from breeding populations. Breeding programs combine desirable traits from two or more cultivars or various broad-based sources into breeding pools from which cultivars are developed by selfing and selection of desired phenotypes. The new cultivars are evaluated to determine which have commercial potential.

Pedigree breeding is used commonly for the improvement of self-pollinating crops. Two parents which possess favorable, complementary traits are crossed to produce an $F_1$. An $F_2$ population is produced by selfing one or several $F_1$'s. Selection of the best individuals may begin in the $F_2$ population; then, beginning in the $F_3$, the best individuals in the best families are selected. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In a multiple-seed procedure, rice breeders commonly harvest one or more seeds from each plant in a population and thresh them together to form a bulk. Part of the bulk is used to plant the next generation and part is put in reserve. The procedure has been referred to as modified single-seed descent or the pod-bulk technique.

The multiple-seed procedure has been used to save labor at harvest. It is considerably faster to thresh panicles with a machine than to remove one seed from each by hand for the single-seed procedure. The multiple-seed procedure also makes it possible to plant the same number of seeds of a population each generation of inbreeding. Enough seeds are harvested to make up for those plants that did not germinate or produce seed.

Descriptions of other breeding methods that are commonly used for different traits and crops can be found in one of several reference books (e.g., Allard, 1960; Simmonds, 1979; Sneep et al., 1979; Fehr, 1987).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer; for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

Rice, *Oryza sativa L.*, is an important and valuable field crop. Thus, a continuing goal of plant breeders is to develop stable, high yielding rice cultivars that are agronomically sound. The reasons for this goal are obviously to maximize the amount of grain produced on the land used and to supply food for both animals and humans. To accomplish this goal, the rice breeder must select and develop rice plants that have the traits that result in superior cultivars.

SUMMARY OF THE INVENTION

According to the invention, there is provided a novel rice cultivar, designated Calhikari-201. This invention thus relates to the seeds of rice cultivar Calhikari-201, to the plants of rice Calhikari-201 and to methods for producing a rice plant produced by crossing the rice Calhikari-201 with itself or another rice line.

Thus, any such methods using the rice variety Calhikari-201 are part of this invention: selfing, backcrosses, hybrid production, crosses to populations, and the like. All plants produced using rice variety Calhikari-201 as a parent are within the scope of this invention. Advantageously, the rice variety could be used in crosses with other, different, rice plants to produce first generation ($F_1$) rice hybrid seeds and plants with superior characteristics.

In another aspect, the present invention provides for single gene converted plants of Calhikari-201. The single transferred gene may preferably be a dominant or recessive allele. Preferably, the single transferred gene will confer such traits as herbicide resistance, insect resistance, resistance for bacterial, fungal, or viral disease, male fertility, male sterility, enhanced nutritional quality, and industrial usage. The single gene may be a naturally occurring rice gene or a transgene introduced through genetic engineering techniques.

In another aspect, the present invention provides regenerable cells for use in tissue culture of rice plant Calhikari-201. The tissue culture will preferably be capable of regenerating plants having the physiological and morphological characteristics of the foregoing rice plant, and of regenerating plants having substantially the same genotype as the foregoing rice plant. Preferably, the regenerable cells in such tissue cultures will be embryos, protoplasts, meristematic cells, callus, pollen, leaves, anthers, root tips, flowers, seeds, panicles or stems. Still further, the present invention provides rice plants regenerated from the tissue cultures of the invention.

DEFINITIONS

In the description and tables which follow, a number of terms are used. In order to provide a clear and consistent understanding of the specification and claims, including the scope to be given such terms, the following definitions are provided:

Days to 50% Heading. Average number of days from seeding to the day when 50% of all panicles are exerted at least partially through the leaf sheath. A measure of maturity.

Grain Yield. Grain yield is measured in pounds per acre and at 14.0% moisture. Grain yield of rice is determined by the number of panicles per unit area, the number of fertile florets per panicle, and grain weight per floret.

Lodging Percent. Lodging is measured as a subjective rating and is percentage of the plant stems leaning or fallen completely to the ground before harvest.

Grain Length (L). Length of a rice grain is measured in millimeters.

Grain Width (W). Width of a rice grain is measured in millimeters.

Length/Width (L/W) Ratio. This ratio is determined by dividing the average length (L) by the average width (W).

1000 Grain Wt. The weight of 1000 rice grains as measured in grams.

Harvest Moisture. The percent of moisture of the grain when harvested.

Plant Height. Plant height in centimeters is taken from soil surface to the tip of the extended panicle at harvest.

Apparent Amylose Percent. The most important grain characteristic that describes cooking behavior in each grain class, or type, i.e., long, medium and short grain. The percentage of the endosperm starch of milled rice that is amylose. Standard long grains contain 20 to 23% amylose. Rexmont type long grains contain 24 to 25% amylose. Short and medium grains contain 16 to 19% amylose. Waxy rice contains 0% amylose. Amylose values will vary over environments.

Alkali Spreading Value. Indicator of gelatinization temperature and an index that measures the extent of disintegration of milled rice kernel in contact with dilute alkali solution. Standard long grains have 3 to 5 Alkali Spreading Value (intermediate gelatinization temperature).

RVA Viscosity. Rapid Visco Analyzer is a new and widely used laboratory instrument to examine paste viscosity, or thickening ability of milled rice during the cooking process.

Hot Paste Viscosity. Viscosity measure of rice flour/water slurry after being heated to 95° C. Lower values indicate softer and more sticky cooking types of rice.

Cool Paste Viscosity. Viscosity measure of rice flour/water slurry after being heated to 95° C. and uniformly cooled to 50° C. (American Association of Cereal Chemist). Values less than 200 for cool paste indicate softer cooking types of rice.

Allele. Allele is any of one or more alternative forms of a gene, all of which alleles relate to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid $F_1$ with one of the parental genotypes of the $F_1$ hybrid.

Essentially all the Physiological and Morphological Characteristics. A plant having essentially all the physiological and morphological characteristics means a plant having the physiological and morphological characteristics, except for the characteristics derived from the converted gene.

Quantitative Trait Loci (QTL). Quantitative trait loci (QTL) refer to genetic loci that control to some degree numerically representable traits that are usually continuously distributed.

Regeneration. Regeneration refers to the development of a plant from tissue culture.

Single Gene Converted (Conversion). Single gene converted (conversion) plant refers to plants which are developed by a plant breeding technique called backcrossing wherein essentially all of the desired morphological and physiological characteristics of a variety are recovered in addition to the single gene transferred into the variety via the backcrossing technique or via genetic engineering.

DETAILED DESCRIPTION OF THE INVENTION

Rice cultivar Calhikari-201 is a semidwarf, early maturing, pubescent, premium quality short-grain variety that was evaluated from 1996 to 1998. It is a selection from the 1992 cross R18026. Calhikari-201 has the pedigree 'Koshihikari'/(91-Y-157)*2. Koshihikari is a tall, pubescent, late maturing, lodging susceptible, premium quality Japanese short-grain cultivar recognized for its high milling and cooking quality. 91-Y-157 was a RES advanced short-grain breeding line with the pedigree Koshihikari/'S-101'. S-101 is a very early maturing, semidwarf short-grain cultivar developed and released by California Cooperative Rice Research Foundation, Inc. that is no longer in production.

Calhikari-201 is a product of pedigree and backcross breeding. $F_2$ panicle selections were made at RES in 1994 and $F_{3-7}$ progeny rows were grown, selected, and advanced at RES and winter nursery facilities on Kauai, Hawaii. It was identified in a 1994 $F_4$ progeny row, tested in small plots yield tests in 1995, and tested as 96-Y-055 in the University of California Cooperative Extension (UCCE) Statewide Yield Tests from 1996 to 1998.

Panicle selections were first taken for head row production in 1996 and continued through 1998. During the head row production, any putative segregating or variant rows were removed from the field. Visual inspection (seedling vigor, heading date, plant height, grain shape, etc.) of head rows were used as criteria to confirm cultivar purity. This standard procedure is used at RES to monitor and maintain breeder seed of 11 currently grown California rice cultivars. Hawaii winter nursery facilities at the University of Hawaii, Kauai Agricultural Research Center, were used for generation advance and seed increase. An awnless head row component was selected from 1000 head rows in 1997 and panicles advanced in the winter nursery in 1997 to 1998. The 1998 head row seed from the winter nursery was used with the 1997 awnless component to plant 2.9 acres of foundation seed in 1998. Head rows from 500 single panicles were also planted in the foundation field and bulked for breeder seed. Calhikari-201 was inspected and approved for certification by the California Crop Improvement Association in 1998. Classes of seed will be breeder, foundation, registered, and certified seed produced in California. Foundation seed can be used to produce foundation seed if necessary and head row and breeder seed will be produced in foundation fields as necessary to maintain cultivar purity. Calhikari-201 has been observed in seed increase and production fields for three generations (1997 to 1998) and found to be uniform and stable.

The cultivar has shown uniformity and stability, as described in the following variety description information. It has been self-pollinated a sufficient number of generations with careful attention to uniformity of plant type. The line has been increased with continued observation for uniformity.

Rice Cultivar Calhikari-201 has the following morphologic and other characteristics (based primarily on data collected at Biggs, Calif.).

VARIETY DESCRIPTION INFORMATION

1. MATURITY (Biggs, Calif. at 135 kg N/ha)
   Days to maturity: 84
   14 days earlier than Koshihikari
   3 days later than Akitakomachi Maturity Class (50% heading-California): Early (91–97days)
2. CULM (Degrees from perpendicular after flowering)
   Angle: Intermediate (less than 45°)
   Length: 90.0 cm (Soil level to top of extended panicle on main stem)
   Shorter than Koshihikari by 25.0 cm
   Longer than L-203 by 5.0 cm
   Height Class: Semidwarf
   Internode Color (After flowering): Green
   Strength (Lodging resistance): Intermediate (most plants lodged)
3. FLAG LEAF (After Heading)
   Length: 26.7 cm
   Width: 9.5 mm
   Pubescence: Pubescent
   Leaf Angle (After heading): Intermediate
   Blade Color: Green
   Basal Leaf Sheath Color: Green
4. LIGULE
   Length (From base of collar to the tip, at late vegetative stage): 7.0 mm
   Color (Late vegetative state): White
   Shape: Cleft
   Collar Color (Late vegetative stage): Pale green
   Auricle Color (Late vegetative stage): Pale green
5. PANICLE
   Length: 15.5 cm
   Type: Intermediate
   Secondary Branching: Light
   Exsertion (near maturity): 90–99%
   Axis: Droopy
   Shattering: Very low (less than 1 %)
   Threshability: Difficult
6. GRAIN (Spikelet)
   Awns (After full heading): Short and partly awned
   Apiculus Color (At maturity): Straw Stigma Color: White
Lemma and Palea Color (At maturity): Straw
Lemma and Palea Pubescence: Short hairs
Spikelet Sterility (At maturity): Highly fertile (>90%)
7. GRAIN (Seed)
  Seed Coat Color: Light brown
  Endosperm Type: Nonglutinous (nonwaxy)
  Endosperm Translucency: Clear
  Endosperm Chalkiness: Small (less than 10% of sample)
  Scent: Nonscented
  Shape Class (Length/width ratio):
    Paddy-Short (2.2:1 and less)
    Brown-Short (2.0:1 and less)
    Milled-Short (1.9:1 and less)

| Measurements: | | | |
| --- | --- | --- | --- |
| Length (mm) | Width (mm) | L/W Ratio | 1000 Grains (grams) |
| Paddy 7.13 | 3.43 | 2.1 | 26.0 |
| Brown 5.24 | 2.97 | 1.8 | 22.1 |
| Milled 4.81 | 2.86 | 1.7 | 19.3 |

Milling Yield (% whole kernel (head) rice to rough rice): 65:69
Protein: 5.8%
Amylose: 18%
Gelatinization Temperature Type: Low
Amylographic Paste Viscosity (Rapid Visco Amylograph—RVU)

| | |
| --- | --- |
| Peak | 313 |
| Hot Paste | 193 |
| Cooled Paste | 306 |
| 'Breakdown' | 120 |
| 'Setback' | 114 |

8. RESISTANCE TO LOW TEMPERATURE
  Germination and Seedling Vigor: High
  Flowering (Spikelet fertility): Medium
9. SEEDLING VIGOR NOT RELATED TO LOW TEMPERATURE
  Vigor: High
10. DISEASE RESISTANCE
  Aggregate Sheath Spot *Rhizoctonia oryzae-sativae*: Mod. Susceptible
  Stem Rot *Scierotium oryzae*: Mod. Susceptible
11. INSECT RESISTANCE
  Rice Water Weevil *Lissorhoptrus oryzophilus*: Susceptible This invention is also directed to methods for producing a rice plant by crossing a first parent rice plant with a second parent rice plant, wherein the first or second rice plant is the rice plant from the line Calhikari-201. Further, both first and second parent rice plants may be from the cultivar Calhikari-201. Therefore, any methods using the cultivar Calhikari-201 are part of this invention: selfing, backcrosses, hybrid breeding, and crosses to populations. Any plants produced using cultivar Calhikari-201 as a parent are within the scope of this invention.

As used herein, the term "plant" includes plant cells, plant protoplasts, plant cells of tissue culture from which rice plants can be regenerated, plant calli, plant clumps, and plant cells that are intact in plants or parts of plants, such as pollen, flowers, embryos, ovules, seeds, pods, leaves, stems, anthers and the like. Thus, another aspect of this invention is to provide for cells which upon growth and differentiation produce a cultivar having essentially all of the physiological and morphological characteristics of Calhikari-201.

Culture for expressing desired structural genes and cultured cells are known in the art. Also as known in the art, rice is transformable and regenerable such that whole plants containing and expressing desired genes under regulatory control may be obtained. General descriptions of plant expression vectors and reporter genes and transformation protocols can be found in Gruber, et al., "Vectors for Plant Transformation, in Methods in Plant Molecular Biology & Biotechnology" in Glich, et al., (Eds. pp. 89–119, CRC Press, 1993). Moreover GUS expression vectors and GUS gene cassettes are available from Clone Tech Laboratories, Inc., Palo Alto, Calif. while luciferase expression vectors and luciferase gene cassettes are available from Pro Mega Corp. (Madison, Wis.). General methods of culturing plant tissues are provided for example by Maki, et al., "Procedures for Introducing Foreign DNA into Plants" in Methods in Plant Molecular Biology & Biotechnology, Glich, et al., (Eds. pp. 67–88 CRC Press, 1993); and by Phillips, et al., "Cell-Tissue Culture and In-Vitro Manipulation" in Corn & Corn Improvement, 3rd Edition; Sprague, et al., (Eds. pp. 345–387) American Society of Agronomy Inc., 1988. Methods of introducing expression vectors into plant tissue include the direct infection or co-cultivation of plant cells with *Agrobacterium tumefaciens*, Horsch et al., Science, 227:1229 (1985). Descriptions of Agrobacterium vectors systems and methods for Agrobacterium-mediated gene transfer provided by Gruber, et al., supra.

Useful methods include but are not limited to expression vectors introduced into plant tissues using a direct gene transfer method such as microprojectile-mediated delivery, DNA injection, electroporation and the like. More preferably expression vectors are introduced into plant tissues using the microprojectile media delivery with the biolistic device Agrobacterium-medicated transformation. Transformant plants obtained with the protoplasm of the invention are intended to be within the scope of this invention.

The present invention contemplates a rice plant regenerated from a tissue culture of a variety (e.g., Calhikari-201) or hybrid plant of the present invention. As is well known in the art, tissue culture of rice can be used for the in vitro regeneration of a rice plant. Tissue culture of various tissues of rices and regeneration of plants therefrom is well known and widely published. For example, reference may be had to Chu, Q. R., et al., (1999) "Use of bridging parents with high anther culturability to improve plant regeneration and breeding value in rice", Rice Biotechnology Quarterly 38:25–26; Chu, Q. R., et al., (1998), "A novel plant regeneration medium for rice anther culture of Southern U.S. crosses", Rice Biotechnology Quarterly 35:15–16; Chu, Q. R., et al., (1997), "A novel basal medium for embryogenic callus induction of Southern U.S. crosses", Rice Biotechnology Quarterly 32:19–20; and Oono, K., "Broadening the Genetic Variability By Tissue Culture Methods", Jap. J. Breed. 33 (Suppl.2), 306–307, illus. 1983, the disclosures of which are hereby incorporated herein in their entirety by reference. Thus, another aspect of this invention is to provide cells which upon growth and differentiation produce rice plants having the physiological and morphological characteristics of variety Calhikari-201.

TABLES

TABLE 1

Agronomic characteristics and performance of Calhikari-201 and Akitakomachi Statewide Yield Tests - 1996 to 1998

|  | Akitakomachi | Calhikari-201 |
|---|---|---|
| Seedling vigor score† | 3.8* | 4.5 |
| Days to 50% heading | 82* | 90 |
| Plant height (cm) | 101* | 88 |
| Lodging (%) | 97* | 40 |
| Grain Moisture at harvest (%) | 19.4* | 19.0 |
| Grain yield at 14% Moisture (lb/acre) | 6390* | 8200 |

*Significantly different from Calhikari-201 according to LSD (0.05)
†Seedling vigor visual score where 1 = poor and 5 = excellent

TABLE 2

Agronomic characteristics and performance of Akitakomachi, Calhikari-201 and Koshihikari Mathews Ranch, Yuba County, CA - 1997–1998

|  | Akitakomachi | Calhikari-201 | Koshihikari |
|---|---|---|---|
| Seedling vigor score† | 3.7* | 4.9 | 4.8 |
| Days to 50% heading | 86* | 91 | 100* |
| Plant height (cm) | 97* | 87 | 106* |
| Lodging (%) | 80* | 0 | 90* |
| Grain Moisture at harvest (%) | 20.8 | 18.5 | 21.7 |
| Grain yield at 14% Moisture (lb/acre) | 6290* | 7430 | 5700* |

*Significantly different from Calhikari-201 according to LSD (0.05)
†Seedling vigor visual score where 1 = poor and 5 = excellent

TABLE 3

Grain yield comparison
Large plot yield tests - 1996–1998
Pounds per Acre

| Location | Year | Akitakomachi | Calhikari-201 |
|---|---|---|---|
| RES | 1996 | 5732 | 8430* |
| RES | 1997 | 7290 | 9460* |
| San Joaquin | 1997 | 7280 | 7030 |
| Sutter | 1997 | 7570 | 9080* |
| Yolo | 1997 | 6430 | 10270* |
| RES | 1998 | 6140 | 8270* |
| San Joaquin | 1998 | 6140 | 6990* |
| Sutter | 1998 | 4860 | 5710 |
| Yolo | 1998 | 6030 | 8560* |

*Significantly different from Akitakomachi according to LSD (0.05)

When the term rice plant is used in the context of the present invention, this also includes any single gene conversions of that variety. The term single gene converted plant as used herein refers to those rice plants which are developed by a plant breeding technique called backcrossing or via genetic engineering techniques wherein essentially all of the desired morphological and physiological characteristics of a variety are recovered in addition to the single gene transferred into the variety via the backcrossing technique or via genetic engineering. Backcrossing methods can be used with the present invention to improve or introduce a characteristic into the variety. The term backcrossing as used herein refers to the repeated crossing of a hybrid progeny back to the recurrent parent. The parental rice plant which contributes the gene for the desired characteristic is termed the nonrecurrent or donor parent. This terminology refers to the fact that the nonrecurrent parent is used one time in the backcross protocol and therefore does not recur. The parental rice plant to which the gene or genes from the nonrecurrent parent are transferred is known as the recurrent parent as it is used for several rounds in the backcrossing protocol (Poehlman & Sleper, 1994; Fehr, 1987). In a typical backcross protocol, the original variety of interest (recurrent parent) is crossed to a second variety (nonrecurrent parent) ithat carries the single gene of interest to be transferred. The resulting progeny from this cross are then crossed again to the recurrent parent and the process is repeated until a rice plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original variety. To accomplish this, a single gene of the recurrent variety is modified or substituted with the desired gene from the nonrecurrent parent, while retaining essentially all of the rest of the desired genetic, and therefore the desired physiological and morphological, constitution of the original variety. The choice of the particular nonrecurrent parent will depend on the purpose of the backcross, one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new variety but that can be improved by backcrossing techniques. Single gene traits may or may not be transgenic, examples of these traits include but are not limited to, male sterility, herbicide resistance, resistance for bacterial, fungal, or viral disease, insect resistance, male fertility, enhanced nutritional quality, industrial usage, yield stability and yield enhancement. These genes are generally inherited through the nucleus.

DEPOSIT INFORMATION

A deposit of the California Cooperative Rice Research Foundation proprietary rice cultivar Calhikari-201 disclosed above and recited in the appended claims has been made with the American Type Culture Collection (ATCC), 10801 University Boulevard, Manassas, Va. 20110. The date of deposit was May 21, 2001. The deposit of 2,500 seeds were taken from the same deposit maintained by the California Cooperative Rice Research Foundation since prior to the filing date of this application. All restrictions upon the deposit have been removed, and the deposit is intended to meet all of the requirements of 37 C.F.R. §1.801–1.809. The ATCC accession number is PTA-3394. The deposit will be maintained in the depository for a period of 30 years, or 5 years after the last request, or for the effective life of the patent, whichever is longer, and will be replaced as necessary during that period.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. A rice seed designated Calhikari-201, wherein a representative sample of said seed has been deposited under ATCC Accession No. PTA-3394.

2. A plant, or its parts, produced by growing the seed of claim 1.

3. Pollen of the plant of claim 2.

4. An ovule of the plant of claim 2.

5. A rice plant having all of the physiological and morphological characteristics of the rice plant of claim 2, or its parts.

6. Tissue culture of the seed of claim 1.

7. A rice plant regenerated from the tissue culture of claim 6.

8. Tissue culture, protoplasts or calli of regenerable cells of the plant, or its parts, of claim 2.

9. The tissue culture, calli or protoplasts of claim 8 wherein the regenerable cells are from embryos, meristems, pollen, leaves, anthers, roots, root tips, flowers, seeds, or stems.

10. A rice plant regenerated from the tissue culture of claim 9.

11. A method for producing a rice seed comprising crossing a first parent rice plant with a second parent rice plant and harvesting the resultant hybrid rice seed, wherein said first or second parent rice plant is the rice plant of claim 2.

12. A hybrid rice seed produced by the method of claim 11.

13. A hybrid rice plant, or its parts, produced by growing said hybrid rice seed of claim 12.

14. Rice seed produced from said hybrid rice plant of claim 13.

15. The rice plant, or its parts, produced from the rice seed of claim 14.

16. A rice plant derived from the soybean plant of claim 5 by a single gene conversion.

17. The plant of claim 16, wherein the gene is a gene which is introduced by transgenic method.

18. The plant of claim 16, wherein the gene is a dominant allele.

19. The plant of claim 16, wherein the gene is a recessive allele.

20. The plant of claim 16, wherein the gene confers herbicide resistance.

21. The plant of claim 16, wherein the gene confers insect resistance.

22. The plant of claim 16, wherein the gene confers resistance to bacterial, fungal or viral disease.

23. The plant of claim 16, wherein the gene confers male sterility.

* * * * *